US00PP21399P2

(12) United States Plant Patent
Bergman

(10) Patent No.: US PP21,399 P2
(45) Date of Patent: Oct. 19, 2010

(54) ***CHRYSANTHEMUM* PLANT NAMED 'YOADELLE'**

(50) Latin Name: *Chrysanthemum×morifolium*
Varietal Denomination: Yoadelle

(75) Inventor: Wendy Bergman, Lehigh Acres, FL (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/586,554

(22) Filed: Sep. 24, 2009

(51) Int. Cl.
*A01H 5/00* (2006.01)

(52) U.S. Cl. ..... Plt./294

(58) Field of Classification Search ..... Plt./294
See application file for complete search history.

*Primary Examiner*—Annette H Para
(74) *Attorney, Agent, or Firm*—S. Matthew Edwards

(57) ABSTRACT

A new *Chrysanthemum* plant named 'Yoadelle,' particularly distinguished by the small single white spoon shaped ray florets, compact and short, uniform habit with excellent branching, and dark, glossy small foliage.

1 Drawing Sheet

Latin name of the genus and species of the plant claimed: *Chrysanthemum×morifolium.*

Varietal denomination: 'Yoadelle'.

BACKGROUND OF THE NEW PLANT

The present invention comprises a new *Chrysanthemum*, botanically known as *Chrysanthemum×morifolium*, and hereinafter referred to by the variety name 'Yoadelle'.

'Yoadelle' is a product of a planned breeding program. The new cultivar has small single white spoon shaped ray florets, compact and short, uniform habit with excellent branching; dark, glossy small foliage.

'Yoadelle' originated from a hybridization made in February 2004 in a controlled breeding environment in Salinas, Calif. The female parent was the proprietary plant designated 'YB-A0900,' unpatented, with white daisy spoon flowers. 'YB-A0900' has more floriferiousness, is taller and has a less compact habit than 'Yoadelle'.

The male parent of 'Yoadelle' was the proprietary plant designated as 'YB-A7015,' unpatented, with white anemone spoon flower form. 'YB-A7015' has less floriferiousness and a less compact habit than 'Yoadelle'.

'Yoadelle' was selected as one flowering plant within the progeny of the stated cross in February 2005, grown outdoors in a field covered by saran in Fort Myers, Fla.

The first act of asexual reproduction of 'Yoadelle' was accomplished when vegetative cuttings were propagated from the initial selection in May 2005, in a controlled environment in Fort Myers, Fla.

Horticultural examination of plants grown from cuttings of the plant initiated in May 2005, and continuing thereafter, has demonstrated that the combination of characteristics as herein disclosed for 'Yoadelle' are firmly fixed and are retained through successive generations of asexual reproduction.

'Yoadelle' has not been observed under all possible environmental conditions. The phenotype may vary significantly with variations in environment such as temperature, light intensity and day length.

A Plant Breeder's Right for this cultivar was applied for in Canada in October 2008. 'Yoadelle' has not been made publicly available more than one year prior to the filing of this application.

BRIEF DESCRIPTION OF THE PHOTOGRAPHS

The accompanying photographic drawing shows typical flower and foliage characteristics of 'Yoadelle' with colors being as true as possible with an illustration of this type. The photographic drawing shows 3 flowering potted plants of the new variety, with a close-up of the flowers.

DETAILED BOTANICAL DESCRIPTION

The plant descriptions, measurements and aforementioned photographs were taken in Gilroy, Calif. in April 2009, under greenhouse conditions. The plants were started and grown in central coastal California, grown under conditions which approximate those generally used in commercial potted *Chrysanthemum* production and were about 8-9 weeks of age when shipped to Gilroy, Calif. in April 2009.

Color references are made to The Royal Horticultural Society Colour Chart (R.H.S.) 2001.

BRIEF SUMMARY OF INVENTION

The following traits have been repeatedly observed and are determined to be basic characteristics of the new variety. The combination of these characteristics distinguishes this *Chrysanthemum* as a new and distinct variety.

TABLE 1

DIFFERENCES BETWEEN THE NEW VARIETY 'YOADELLE' AND A SIMILAR VARIETY

| | 'Yoadelle' | 'Yosylvie' (U.S. Plant Pat. No. 13,035) |
|---|---|---|
| Floret type | Spoon | Regular flat |
| Stem strength | Very strong | Moderately strong |
| Foliage color | Darker | Lighter |

Plant:

*Form, growth and habit.*—Herbaceous pot-type, short and compact habit, stems upright and outwardly spreading, freely branching.

*Plant height.*—8-10 cm.

*Plant height* (*inflorescence included*).—11-12.5 cm.
*Plant width.*—12-14 cm.
*Quantity of short days to flowering* (*response time*).—40-45 days.

Roots:
*Number of days to initiate roots.*—About 4 days at about 22 degrees C.
*Number of days to produce a rooted cutting.*—About 10 days at 22 degrees C.
*Type.*—Fine, fibrous, free branching.
*Color.*—RHS N155B but whiter.

Foliage:
*Arrangement.*—Alternate, simple.
*Immature, leaf color, upper surface.*—Closest to RHS 137A.
*Lower surface.*—RHS 137C.
*Mature, leaf color, upper surface.*—Closest to 137A.
*Lower surface.*—RHS 137C.
*Length.*—3.9-4.3 cm.
*Width.*—2.1-2.2 cm.
*Shape.*—Ovate.
*Base shape.*—Attenuate.
*Apex shape.*—Acute.
*Margin.*—Somewhat palmately lobed; slightly serrate.
*Texture, upper surface.*—Bi-fid T-shaped hairs.
*Lower surface.*—Bi-fid T-shaped hairs.
*Color of veins, upper surface.*—RHS 144A to RHS144B.
*Color of veins, lower surface.*—RHS 144B.
*Petiole color.*—RHS 144B.
*Length.*—0.8-1.2 cm.
*Diameter.*—0.2 cm.
*Texture.*—Bi-fid T-shaped hairs.

Stem:
*Quantity of main branches per plant.*—3-6 with many more secondary.
*Quantity of leaves per branch.*—6.
*Color of stem.*—RHS 146B.
*Length of stem.*—6-8 cm.
*Diameter.*—0.25-0.3 cm.
*Length of internodes.*—0.3-0.9 cm.
*Texture.*—Bi-fid T-shaped hairs.
*Color of peduncle.*—RHS 146B.
*Length of peduncle.*—2-4 cm.
*Peduncle diameter.*—0.1-0.15 cm.
*Texture.*—Bi-fid T-shaped hairs.

Inflorescence:
*Type.*—Composite type, solitary inflorescences (daisy-type) borne terminally above foliage, ray florets arranged acropetally on a capitulum.
*Blooming habit.*—Excellent year round performance.
*Quantity of inflorescences per plant.*—10-15.
*Lastingness of individual blooms on the plant.*—About 34 days.
*Fragrance.*—Slight.

Bud: These plants had no buds with which to describe and measure.

Immature inflorescence:
*Diameter.*—2.5-2.8 cm.
*Color of ray florets, upper surface.*—RHS 155B, but whiter.
*Lower surface.*—RHS 155B, but whiter.

Mature inflorescence:
*Diameter.*—3.7-4.1 cm.
*Total diameter of 'disc'.*—1.5-1.6 cm.

Ray florets:
*Average quantity of florets.*—22-24.
*Color of florets, upper surface.*—RHS 155B, but whiter.
*Lower surface.*—RHS 155B, but whiter.
*Length.*—1.8-1.9 cm.
*Width.*—0.3-0.5 cm at widest.
*Shape.*—Enlongated oblanceolate, so that nearly the entire margins are folded over and fused together to form a spoon, leaving the apex portion free.
*Apex shape.*—Most rounded to obtuse, some slightly retuse.
*Margin.*—Entire.
*Texture, upper surface.*—Papillose.
*Lower surface.*—Papillose.

Disc florets:
*Average quantity of florets.*—150.
*Color of florets.*—RHS 1B, with RHS 12A apices.
*Length.*—0.4-0.5 cm.
*Width.*—0.1 cm.
*Shape.*—Tubular, enlongated.
*Apex shape.*—Acute, 5 pointed.

Phyllaries:
*Quantity.*—15-20.
*Color, upper surface.*—RHS 137A.
*Lower surface.*—RHS 137A but can appear lighter with all the hairs.
*Length.*—0.2-0.3 cm.
*Width.*—0.1 cm.
*Shape.*—Ovate.
*Apex shape.*—Acute.
*Based.*—Fused.
*Margins.*—Entire.
*Texture, upper surface.*—Bi-fid T-shaped hairs.
*Lower surface.*—Bi-fid T-shaped hairs.

Reproductive organs:
*Pistil.*—1.
*Length* (*cm*).—0.6 cm.
*Style color.*—RHS 1B basally, 1C centrally.
*Style length* (*cm*).—0.5 cm.
*Stigma color.*—RHS 12A.
*Stigma shape.*—Bi-parted, some are nearly tri-parted.
*Ovary color.*—RHS 155C.
*Stamens.*—1.
*Color of filaments.*—RHS 1B to RHS 1C.
*Length filaments.*—0.3-0.4 cm.
*Anther color.*—RHS 13B.
*Color of pollen.*—RHS 14B.
*Pollen amount.*—Scarce.
*Fertility/seed set.*—Has not been observed on this hybrid.

Disease/pest resistance: Disease resistance or susceptibility has not been observed on this hybrid.

What is claimed is:

1. A new and distinct variety of *Chrysanthemum* plant named 'Yoadelle,' substantially as illustrated and described herein.

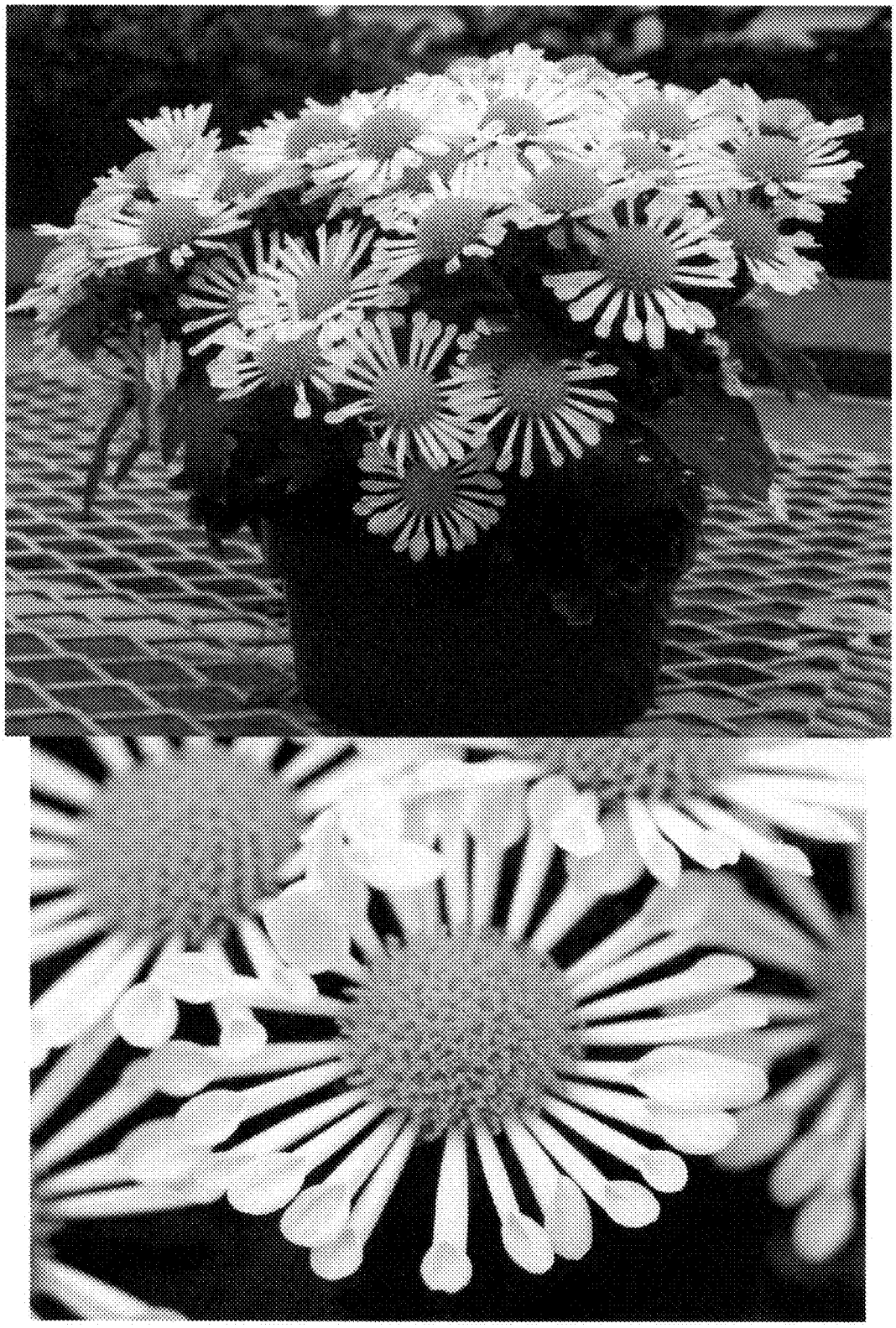

* * * * *